United States Patent
Daynes et al.

(10) Patent No.: US 6,920,354 B2
(45) Date of Patent: Jul. 19, 2005

(54) DEFIBRILLATOR WITH A MULTIPLE-MODE INTERFACE

(75) Inventors: John C. Daynes, Redmond, WA (US); Cathlene D. Buchanan, Shoreline, WA (US); Douglas J. Hill, Newcastle, WA (US); Richard M. Lee, Kirkland, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

(21) Appl. No.: 10/725,704

(22) Filed: Dec. 2, 2003

(65) Prior Publication Data

US 2004/0111122 A1 Jun. 10, 2004

Related U.S. Application Data

(63) Continuation of application No. 09/945,333, filed on Aug. 31, 2001, now Pat. No. 6,754,526.
(60) Provisional application No. 60/248,184, filed on Nov. 13, 2000.

(51) Int. Cl.[7] .................................................. A61N 1/39
(52) U.S. Cl. .......................................................... 607/5
(58) Field of Search ............................ 607/2, 4–8, 31, 607/35, 36; 600/522, 525; D24/185–187

(56) References Cited

U.S. PATENT DOCUMENTS

| | | |
|---|---|---|
| 4,512,253 A | 4/1985 | La Barge et al. |
| 4,837,731 A | 6/1989 | Levine et al. |
| 5,025,206 A | 6/1991 | Germer et al. |
| 5,213,380 A | 5/1993 | Thometschek et al. |
| 5,464,428 A | 11/1995 | Hill |
| D366,258 S | 1/1996 | Fraser et al. |
| 5,630,211 A | 5/1997 | Nagai |
| 5,868,794 A | 2/1999 | Barkley et al. |
| 5,935,152 A | 8/1999 | Merry et al. |
| 6,021,349 A | 2/2000 | Arand et al. |
| D442,692 S | 5/2001 | Salvatori et al. |
| 6,243,819 B1 | 6/2001 | Jung |
| 6,266,562 B1 | 7/2001 | Leyde |
| 6,292,692 B1 | 9/2001 | Skelton et al. |

FOREIGN PATENT DOCUMENTS

GB 2 341 103 A 3/2000

OTHER PUBLICATIONS

"LIFEPAK®2, Portable Battery Operated Defibrillator and Cardioscope," *Product Sheet*, Physio–Control Corp., at least as early as 1972.
"LIFEPAK®3, Portable Battery Operated Cardioscope/Defibrillator," *Product Sheet*, Physio–Control Corp., at least as early as 1972.
"LIFEPAK®4, Portable Battery Operated Cardioscope/Defibrillator with ECG Recorder," *Product Sheet*, Physio–Control Corp., at least as early as 1974.
"LIFEPAK®300, Automatic Advisory Defibrillator," *Service Manual*, Physio–Control Corp., Apr. 1994.

*Primary Examiner*—Jeffrey R. Jastrzab
(74) *Attorney, Agent, or Firm*—Shumaker & Sieffert, P.A.

(57) ABSTRACT

The present invention is directed to a defibrillator having both a manual and an AED mode with corresponding user commands for both modes. The defibrillator includes a door which conceals manual mode commands, such that opening of the door puts the defibrillator in the manual mode and simultaneously reveals the manual mode command buttons. In one actual embodiment, the door includes apertures which allow access to the AED command buttons. When the door is in the open position, a keypad is revealed having manual commands which preferably take the form of buttons. In another actual embodiment, the door includes a switch which senses when the door is opened and sends the defibrillator into manual mode. The door includes a front side having AED command buttons, and a back side having manual mode command buttons. The door conceals a keypad having further manual mode command buttons.

14 Claims, 11 Drawing Sheets

DEFIBRILLATOR WITH A MULTIPLE-MODE INTERFACE

This application is a continuation of U.S. application Ser. No. 09/945,333, filed Aug. 31, 2001 now U.S. Pat. No. 6,754,526, which claims the benefit of U.S. Provisional Application No. 60/248,184, filed Nov. 13, 2000, the entire contents of both of which are incorporated herein by reference.

FIELD OF THE INVENTION

This invention relates to a defibrillator, and more particularly, to a defibrillator having a multiple-mode interface which enables a user to operate the defibrillator in an AED mode or switch quickly to a manual mode.

BACKGROUND OF THE INVENTION

It is well known that the probability of surviving a heart attack often depends critically on the speed with which appropriate medical care is provided. One of the most common and life threatening consequences of a heart attack is the development of a cardiac arrhythmia such as ventricular fibrillation in which the heart is unable to pump a significant volume of blood. When such an arrhythmia occurs, serious brain damage and death may result unless a normal heart rhythm can be restored within a few minutes. The most effective treatment for ventricular fibrillation is the application of a strong electric shock to the patient. Such an electric shock frequently terminates the chaotic activity characteristic of arrhythmia's, and restores the normal pumping action of the heart. Defibrillators for producing and delivering such shocks have been known and successfully used for many years. However, the size and cost of prior defibrillators, coupled with the risk they pose if used improperly, have restricted the use of defibrillators to hospitals and to emergency medical facilities. Many lives would be saved each year if defibrillators could be made more immediately available to heart attack victims.

The advances made in electronics have enabled the production of small, lightweight, and automatic defibrillators, which are portable enough to be hand carried along with a patient while the patient is being transported on a gurney. Defibrillators have also become available in many public gathering places. With such a proliferation of these life-saving devices, there is a need for a defibrillator which may be used by inexperienced as well as highly qualified individuals. Automated external defibrillators (AEDs), as they are called, are designed with an infrequent practitioner in mind. AEDs typically have a simplified routine which attempts to make even a nonpractitioner confident with using the defibrillator with only a modicum of basic training. Most AEDs generally operate in a "semi-automatic mode." For example, the LIFEPAK® 500 AED manufactured by Medtronic Physio-Control Corp. and the FORERUNNER™ AED manufactured by Agilent Technologies have at least two command buttons: (1) an "on" button, and (2) a shock button which delivers a defibrillation pulse to the patient. In addition, the LIFEPAK® 500 AED includes a third button that prompts the AED to analyze the patient to determine whether shock treatment is indicated by monitoring the patient's heart rhythms or electrocardiogram (ECG). Manual delivery of "shock" treatment by pressing a button imparts to the user the seriousness of the event. However, the "shock" button can be eliminated so that the AED delivers the defibrillation pulse to the patient automatically and without human intervention upon detection of a shockable rhythm. Such AEDs are typically referred to as operating in an "automatic" mode. For purposes of the following description, the term "AED mode" may apply to either an automatic or semi-automatic mode.

While the operation of AED controls may appear intuitive, it is to be remembered that AEDs are used in highly stressful situations, where little time for deliberate thought is available. In short, a rescuer must act fast and has little time to decipher the controls on a complicated piece of equipment in which he may have only received basic training. Consequently, the user interface for such AEDs must be as simple and uncluttered as possible. However, AED manufacturers are also striving to provide more sophisticated controls for those highly trained individuals who arrive at the care giving location at a later time. These more experienced personnel are fully comfortable with a defibrillator and an array of many user input commands to more specifically tailor the shock treatment to the patient. Therefore, attempts are being made to combine a simplified or "AED mode" for infrequent rescuers and a "manual mode" for skilled rescuers in one defibrillator apparatus. The goal is to provide a visually uncluttered appearance and somehow differentiate between modes for an infrequent rescuer so as not to befuddle the rescuer, while at the same time providing a host of manual user input commands for the highly trained individual.

Several approaches have been attempted with varying degrees of distinction between manual and AED modes. For example, the LIFEPAK® 300 AED manufactured by Medtronic Physio-Control Corp. can be operated in a semi-automatic mode or a manual mode. To enter the manual mode, the rescuer simply had to press a manual access button located on the front panel of the AED. The remaining buttons on the front panel are soft keys that remain accessible and change function according to the mode of the defibrillator and the corresponding message on the defibrillator's display. Other manufacturers have attempted to use brightly colored or marked command buttons or dials to distinguish between different modes. Unfortunately, in both these approaches, the rescuer is forced to interpret and differentiate between buttons, softkeys and/or displays or otherwise read and process information, in order to operate the device which only increases the possibility of human error.

In U.S. Pat. No. 6,021,349 to Arand et al., an attempt is made to deal with the problem by hiding a "change to manual personality" button behind an access door to prevent accidental depression of the manual button and send the defibrillator into a manual "personality" without the rescuer becoming aware. However, as with the LIFEPAK® 300 AED, the remaining buttons on the front panel of the defibrillator remain accessible and change function according to the mode of the defibrillator and the corresponding message on the defibrillator's display. Consequently, this approach does not solve the problem of providing an uncluttered user interface to prevent the rescuer from having to interpret and distinguish manual command buttons from AED command buttons.

Accordingly, there is a need for a defibrillator having manual, semi-automatic and/or automatic modes which provides a clean and intuitive user interface for selecting, operating, and switching between such modes. However, unintentional shift of the defibrillator from one mode to another should be prevented.

SUMMARY OF THE INVENTION

The present invention is directed to a defibrillator having both a manual and an AED mode with corresponding user commands for both modes. The defibrillator includes a door which conceals manual user commands, such that upon initiating a motion associated with the door, such as activation of a latch or opening of the door, the defibrillator is put into the manual mode, while revealing the manual commands.

In one actual embodiment, the door includes apertures which allow access to the AED mode user commands. The door also includes an assembly with a latch to hold the door in the closed position and an actuator slide the user presses to unlatch and open the door. The actuator slide is accessible while the door is closed. Operation of the actuator slide depresses a button to send the defibrillator into manual mode while the door is closed, and also releases the latch which allows the door to open, concurrently with or slightly after sending the defibrillator into manual mode. When the door is in the open position, a keypad is revealed having manual mode user commands which in one actual embodiment, takes the form of buttons.

In another embodiment, the door includes a switch which senses when the door is open and sends the defibrillator into manual mode. In this embodiment, the door includes a front side having AED mode user command buttons, and a back side having manual mode user command buttons. The back side is visible when the door is opened. The door also conceals a keypad on the defibrillator having further manual mode user commands.

A defibrillator constructed in accordance with the present invention would thus obtain numerous benefits. For example, the defibrillator of the present invention achieves an uncluttered appearance for use by an infrequent user by concealing those commands which are not necessary while the defibrillator is in the AED mode, yet retains more complex features for the more experienced user that can be accessed when the door is opened.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

While the preferred embodiment of the invention has been illustrated and described, it will be appreciated that various changes can be made therein without departing from the spirit and scope of the invention.

Figure 1:
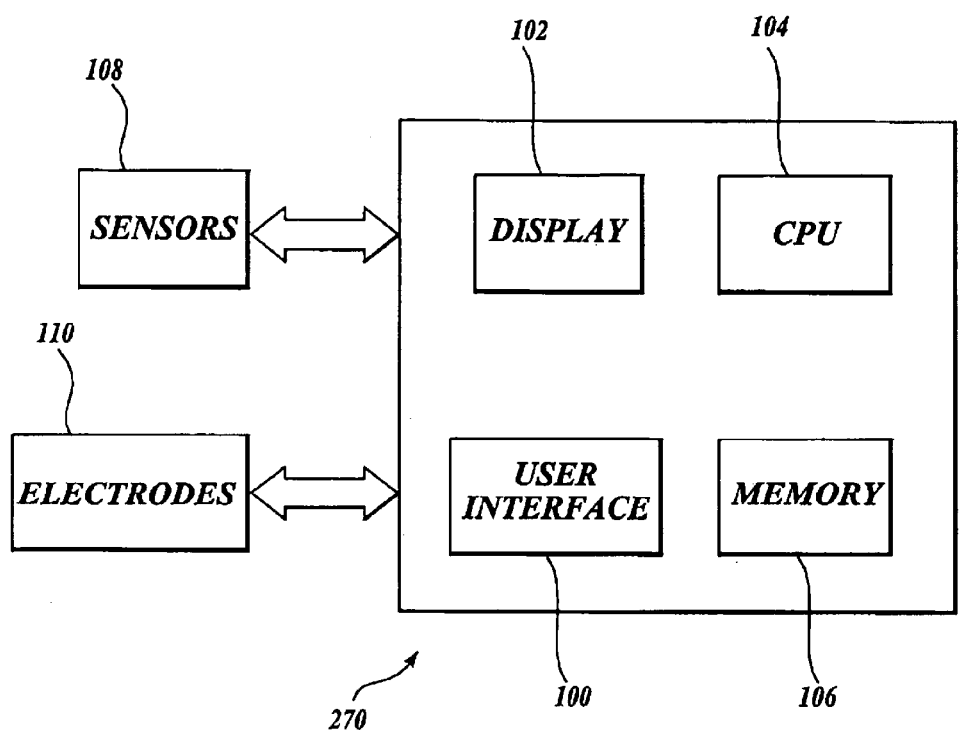
FIG. 1 shows a schematic representation of a defibrillator formed in accordance with the present invention.

FIG. 1 provides a schematic representation of a multiple mode defibrillator 270 having an AED and manual mode which is suitable to use with the present invention. The defibrillator 270 includes a housing containing a user interface panel or keypad 100, the keypad or panel itself having a plurality of user commands. The defibrillator also includes a display screen 102 for communicating instructions to the user or displaying the patient's heart rhythms or other patient or user information. The defibrillator includes a central processing unit 104 ("CPU"), for analyzing and processing the inputs and outputs received from the user, electrodes, periphery hardware and/or other medical accessories and sensors. Periphery hardware (not shown) may include printers, scanners, audio devices such as microphones and speakers, or other computers and the like. The defibrillator includes a memory 106 for storing a set of instructions or programmable algorithms used to carry out the processing of the information in both the manual and the AED modes. The defibrillator further includes sensors and other medical accessories 108 to be attached to a patient to monitor vital signs and other patient parameters, e.g., heart rhythms, $SpO_2$ level, $CO_2$ level, etc. The defibrillator also includes shock therapy delivery devices, such as hard paddles or disposable electrodes, to deliver a therapeutic electric shock to the patient.

Figure 2:
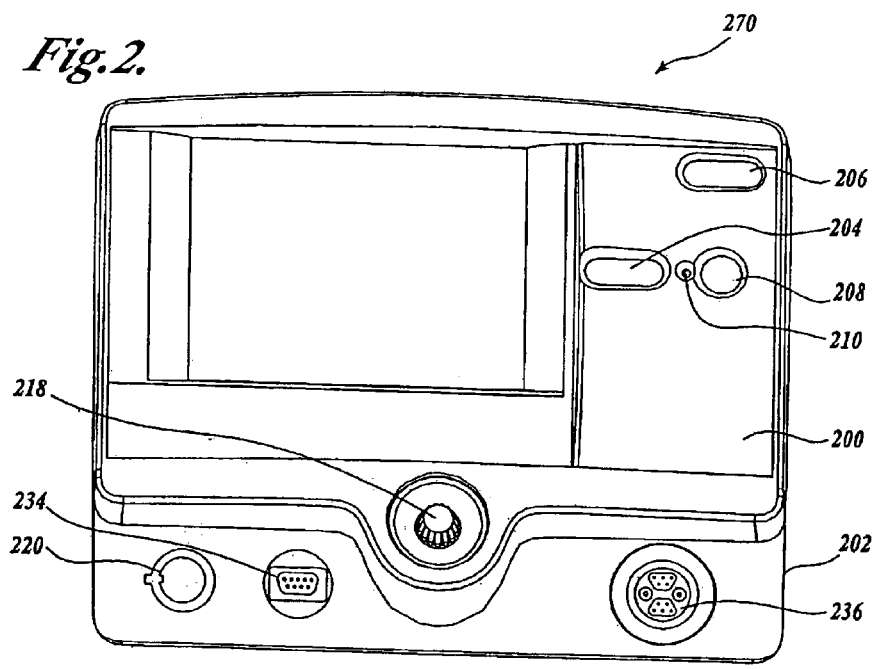
FIG. 2 shows a defibrillator formed in accordance with the present invention showing a door having access to AED mode buttons while the door is closed.
Figure 3:
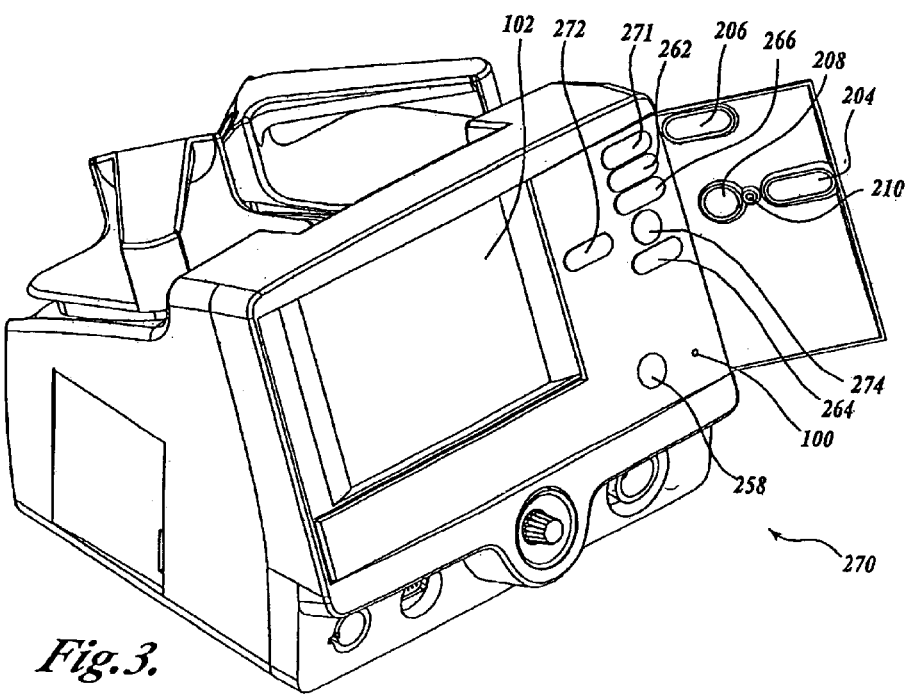
FIG. 3 shows the defibrillator of FIG. 2 when the door is opened, revealing a keypad having manual mode command buttons.

A first actual embodiment of the invention will now be described with reference to FIG. 2. In FIG. 2, the defibrillator 270 includes a door 200 having hinges for attachment to the defibrillator housing 202. The door 200 is removable for maintenance. Certain command buttons located on the user interface panel 100 are visible from the front side of the defibrillator 270 through apertures 204, 206 and 208 provided in the door 200. Referring to FIG. 3, a first command button 271 (visible through aperture 206) may, for instance, be used to power up or power down the defibrillator 270. A second command button 272 (visible through aperture 204) may be used to prompt the defibrillator to analyze the patient's heart rhythm to determine whether shock therapy is indicated. A third command button 274 (visible through aperture 208) may be used to deliver the therapy to the patient. While raised command buttons are illustrated, touch switches may alternately be employed without departing from the spirit and scope of the present invention. As will be described in more detail below, additional command buttons for use in the manual mode are also located on the user interface panel 100, but are hidden from view behind the door 200 when in the closed position. In addition, the defibrillator 270 may also include a knob 218 for gross or fine tuning of information shown on the display monitor 102. The defibrillator includes a port (not shown) for connecting to a second ECG monitor, a serial port (not shown) for connecting to any of a number of peripheral devices and a plug 236 for connecting therapy elements used to delivery therapy to a patent's heart. Although these ports, connectors and input devices are not shown in FIG. 2 as being hidden beneath the door 200, those of ordinary skill in the art will recognize that in other embodiments such components could be located beneath the door so as to further simplify the user interface for the inexperienced rescuer, for example, the ECG and $SpO_2$.

In one actual embodiment, only the user command buttons 271, 272 and 274 are accessible through the apertures 206, 204 and 208 when the defibrillator 270 is in the AED mode. Accordingly, when the defibrillator 270 is powered up and the door 200 is in the closed position, the defibrillator is in the AED mode and only the AED command buttons are visible and accessible to the user. In addition to apertures 206, 204 and 208, the door 200 may also contain at least one aperture 210 for viewing status lights. The status lights may, for instance, indicate that the defibrillator 270 is powered and ready to deliver a shock therapy. It will be appreciated by those of ordinary skill in the art that the door 200 may contain any number of apertures deemed necessary for the industrial design of the defibrillator 270 depending on the number of features, e.g., command buttons, status indicators, etc. that are desired to be revealed to the user. For example, apertures 208 could be removed from the door 200 so as to hide the shock button 274 and provide a user interface for a fully automatic external defibrillator, or in other words, a third mode. Conversely, additional apertures may be provided for revealing additional features, such as a CPR prompt command button for triggering visual and/or aural CPR prompts. In addition to the number of apertures and buttons, those of ordinary skill in the art will also appreciate that the shape, size, configuration and location of the apertures and command buttons on the keypad 100 and/or door 200 may vary without departing from the spirit and scope of the present invention.

Figure 4:
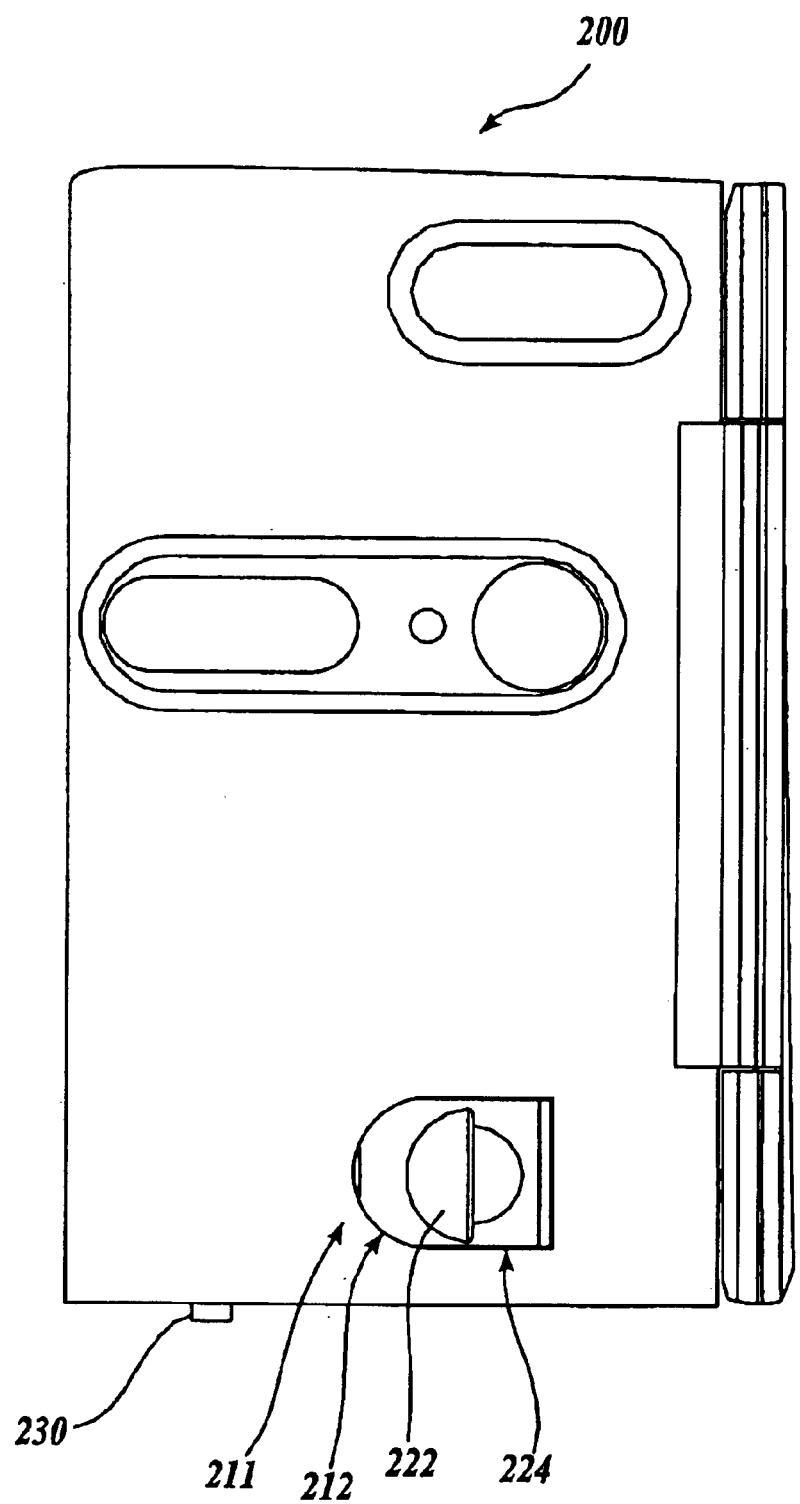
FIG. 4 shows a front plan view of a door constructed in accordance with the present invention.
Figure 5:
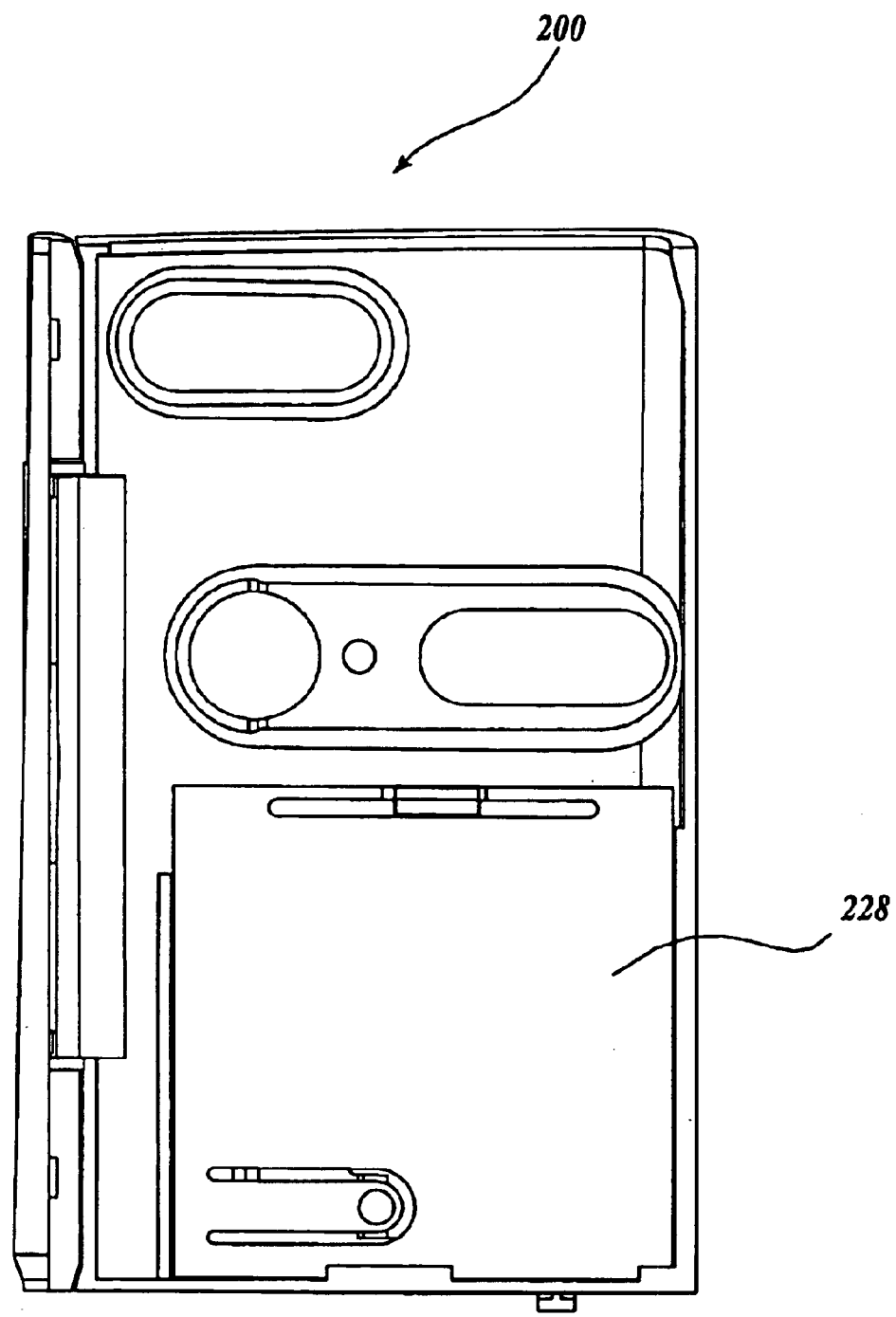
FIG. 5 shows a back plan view of the door of FIG. 4.

Referring now to FIG. 4, the door 200 of the defibrillator 270 illustrated in FIG. 2 is shown in more detail. The door 200 includes an assembly 211 for opening the door 200. The assembly 211 includes an actuator slide 212, a latch 230, and cover 228 (cover 228 is shown in FIG. 5). The front side of actuator slide 212 has a standing rib 222. The user presses the standing rib 222 to release a latch 230, which in turn, opens the door 200. Accordingly, standing rib 222 protrudes through an aperture 224 located on the lower portion of door 200.

Figure 6:
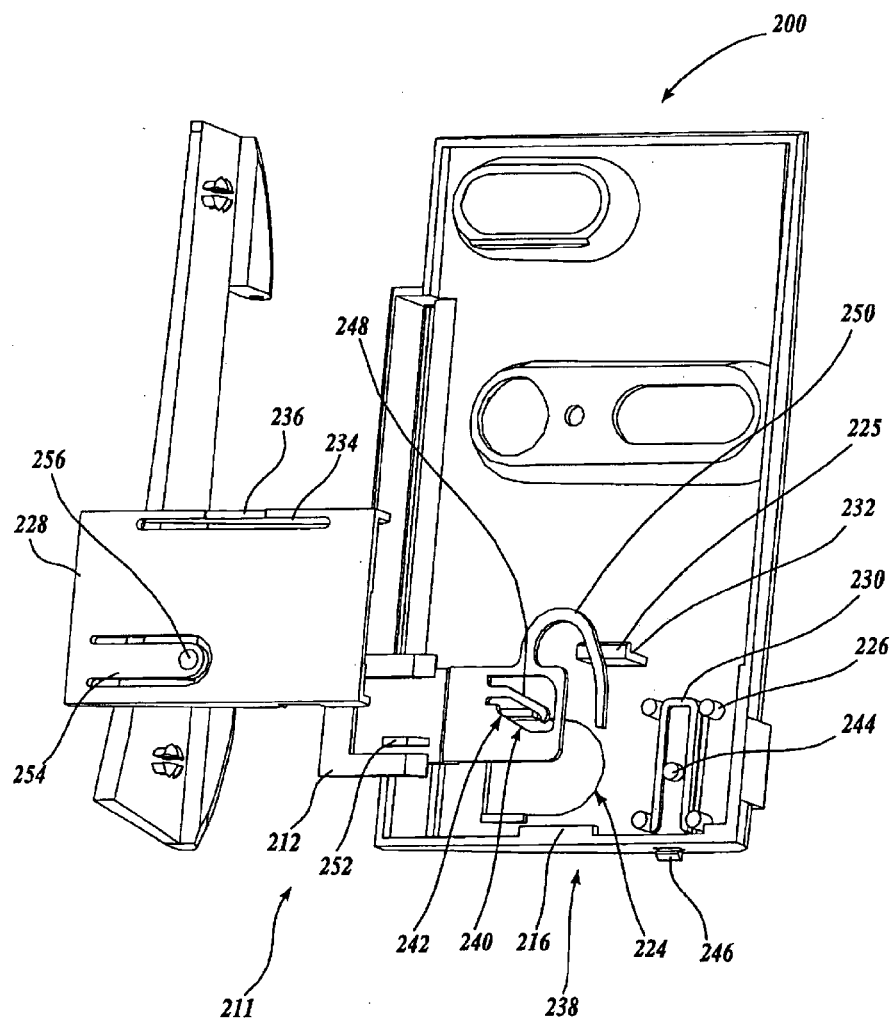
FIG. 6 shows an exploded view of the door of FIG. 4.

Referring now to FIG. 6, an exploded view of an actuator assembly 211 from the back side of door 200, the actuator slide 212, latch 230, and cover 228 are shown. Actuator slide 212 is mounted on door 200, such that the front side of the actuator slide 212 with standing rib 222 faces the back side of door 200 and the standing rib 222 protrudes through the aperture 224 of the door when assembled. Actuator slide 212 is held in place to door 200 by cover 228 which retains the actuator slide within the door 200. Clips 232 and 238 molded onto door 200 retain cover 228 that allows actuator slide 212 to move in a horizontal direction as will be described in more detail below.

The actuator slide 212, cover 228 and latch 230 cooperate with each other to provide a closing mechanism for the door 200. Latch 230 is located on the back side of door 200. Detailing on door 200, such as posts 226, help guide the latch 230 in vertical movement. Latch 230 is held to door 200 by cover 228. Latch 230 includes a chamfer 246 located on the lower end of latch 230 so as to engage a hole in the defibrillator device bezel (not shown) to secure the door 200 in a closed position. Latch 230 also includes a post 244 located approximately in the middle of the latch that engages the actuator slide 212 as will be described in more detail below. Latch 230 is thus constrained to move in a vertical direction by posts 226 on door 200.

The cover 228 is mounted to the door 200 such that actuator slide 212 and latch 230 are substantially concealed by cover 228 as shown in FIG. 6. Cover 228 is held to door 200 by clip 232 located on the back side of door 200. Clip 232 has an upturned lip end 225 that engages a horizontal aperture 234 and a groove 236 on the cover 228. On the bottom edge of door 200, another clip 238 with an upturned lip 216 is provided to retain cover 228 in position, along with clip 232. Thus, cover 228 helps to retain actuator slide 212 and latch 230 in position on the door 200 as shown in FIG. 5.

Returning to FIG. 6, the actuator slide 212 has an angled guide edge 240 formed within an aperture 242 to receive the post 244 of the latch 230. Post 244 is formed from latch 230 and projects outwardly so that a lower surface of the post 244 rides on the upper surface of guide edge 240. As the user presses the standing rib 222 and the actuator slide 212 is moved horizontally in a direction toward the latch 230, the guide edge 240 pushes against post 244. Latch 230, being constrained to move in a vertical direction, rises to raise chamfer 246, thusly releasing the door 200.

Actuator slide 212 also includes spring 248 formed within the aperture 242 that is pushed upward by the latch when door 200 is being closed. Tensioned spring 248 biases latch 230 downward so that latch 230 snaps back forcibly to engage a device bezel. A second spring 250 formed integrally with the actuator slide 212 biases actuator slide 212 away from the latch 230 and opposes movement when the user pushes against the standing rib 222 from the outside of the door 200.

Actuator slide 212 further includes a ramp 252 projecting outwardly from the back side of the slide 212 to face the front side of the cover 228. In turn, cover 228 includes a ramp (not shown) located on a flexible cutout tongue 254 that faces the ramp 252 on actuator slide 212. A hemispherical bump 256 is also located on the flexible cutout tongue 254 on the side opposite of the cover ramp (not shown). Slide ramp 252 and cover ramp (not shown) have angled edges that ride against one another. The cover 228 is stationary as the actuator slide 212 is moved toward latch 230, and the ramps slide against one another, such that flexible tongue 254 moves in a direction away from the door 200 and toward the defibrillator 270. As the actuator slide 212 continues to move toward the latch 230, the bump 256 is further pushed backwards and presses against an unmarked manual mode entry button 258 (FIG. 3) located on the user interface panel 100 of the defibrillator 270. Activation of the manual mode entry button 258 by the assembly 211 while the door 200 is in the closed position places the defibrillator in the manual mode. In one actual embodiment of the present invention, the manual mode button 258 remains unmarked, so as not to confuse the more experienced user upon opening of the door by perhaps providing an indication that an additional button must be pressed to switch modes.

The assembly 211 has four states: (1) When the door 200 is closed, the actuator slide 212 is at the far right of its opening 224 in the door 200, the slide spring 250 is relaxed, and the latch 230 is in an extended position, engaging a hole in the device bezel. (2) When the door 200 is open, the actuator slide 212 is right of its opening 224 in the door 200, the slide spring 250 is relaxed, the latch 230 is in an extended position, and the door may be rotated up to about 270° from its closed position, and is resting against the side of the defibrillator. (3) When the door is being opened, i.e., the actuator slide 212 being moved to the left by the user, the slide 212 is left of its opening 224 in the door, the slide spring 250 is flexed, the ramp 252 on the back of the slide 212 engages with a ramp on the cover 228, causing the tongue 254 to flex, pushing the bump 256 against the manual mode button 258 (FIG. 3). The pressure of the bump 256 on the keypad 100 "pre-loads" the door with an outward force, and the post 244 on the latch 230 has ridden up the angled edge 240 in the actuator slide aperture 242. This moves the latch 230 vertically to its fully raised position, allowing the door 200 to spring open due to the pre-loading of the door. (4) In the fourth state, when the door 200 is being pressed closed by the user, the slide 212 is right of its opening 224 in the door. The slide spring 250 is relaxed, and the chamfer 246 on the latch 230 rides against the device bezel. This causes the latch 230 to move vertically, and post 244 pushes against the spring member 248 in the actuator slide aperture 242. The pressure against the spring member 248 by post 244 causes the latch 230 to return to an extended position as soon as the chamfer 246 moves into line with the hole in the bezel.

Figure 7:
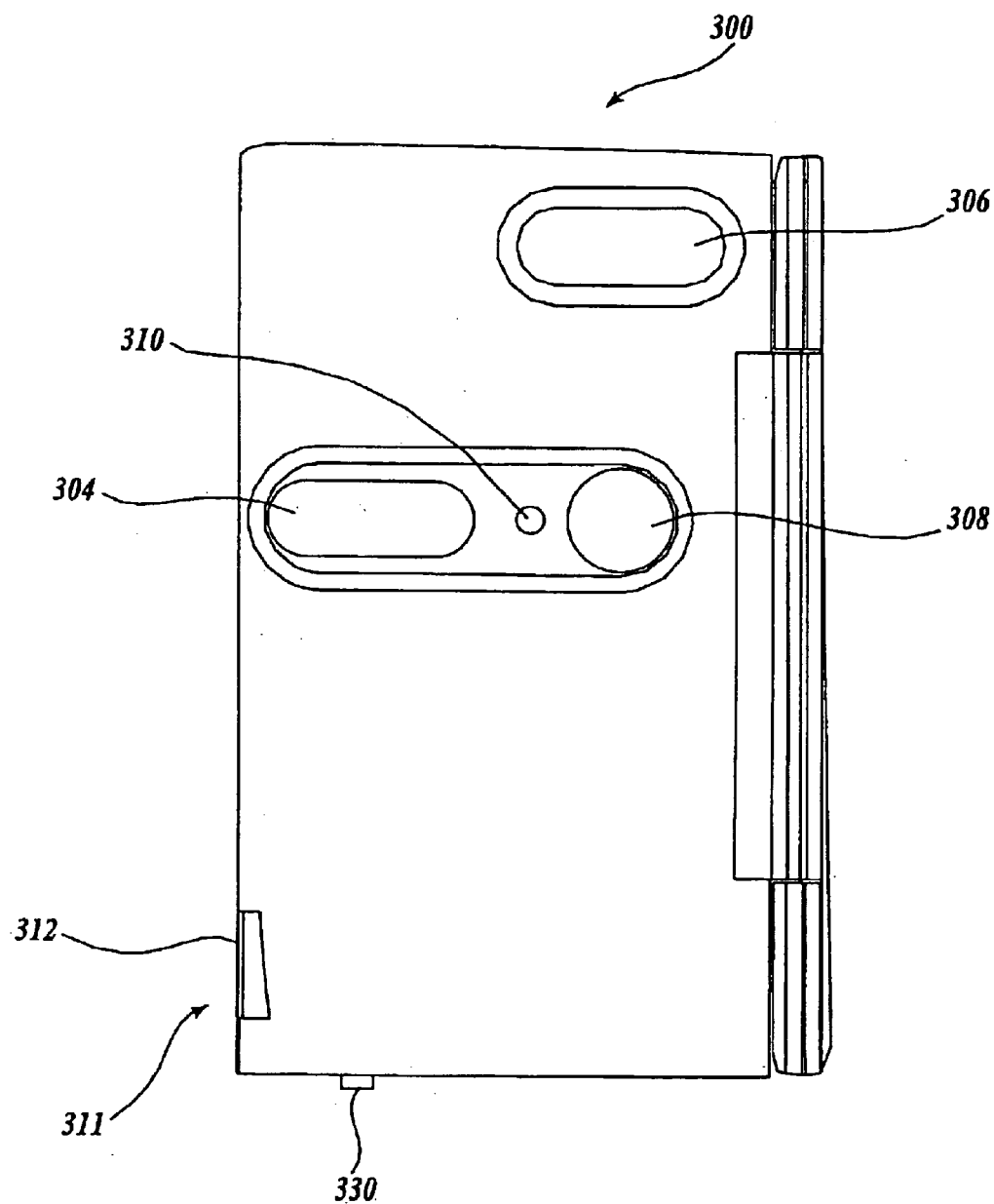
FIG. 7 shows a front plan view of an alternative embodiment of a door constructed in accordance with the present invention.
Figure 8:
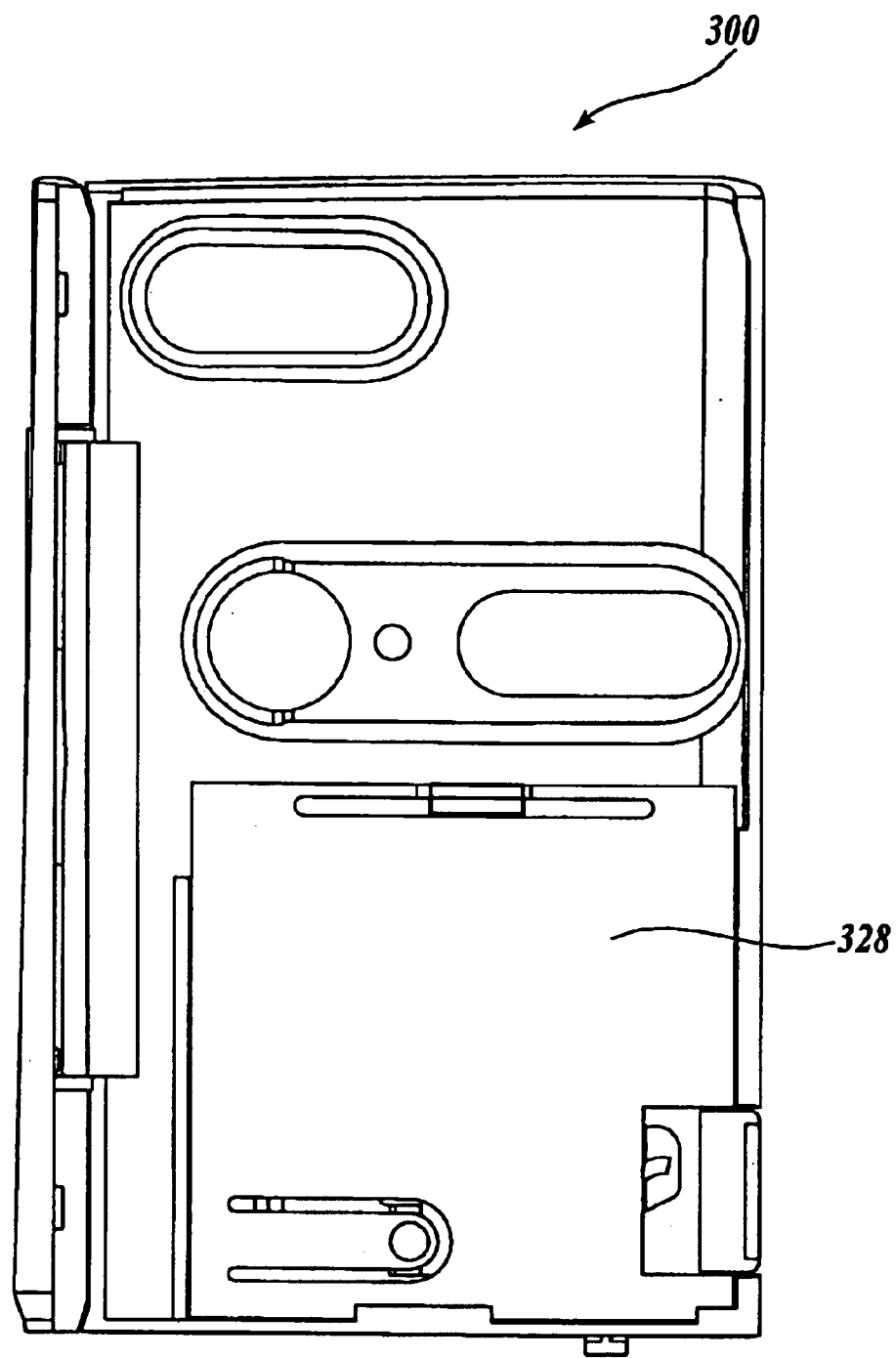
FIG. 8 shows a back plan view of the door of FIG. 7.
Figure 9:
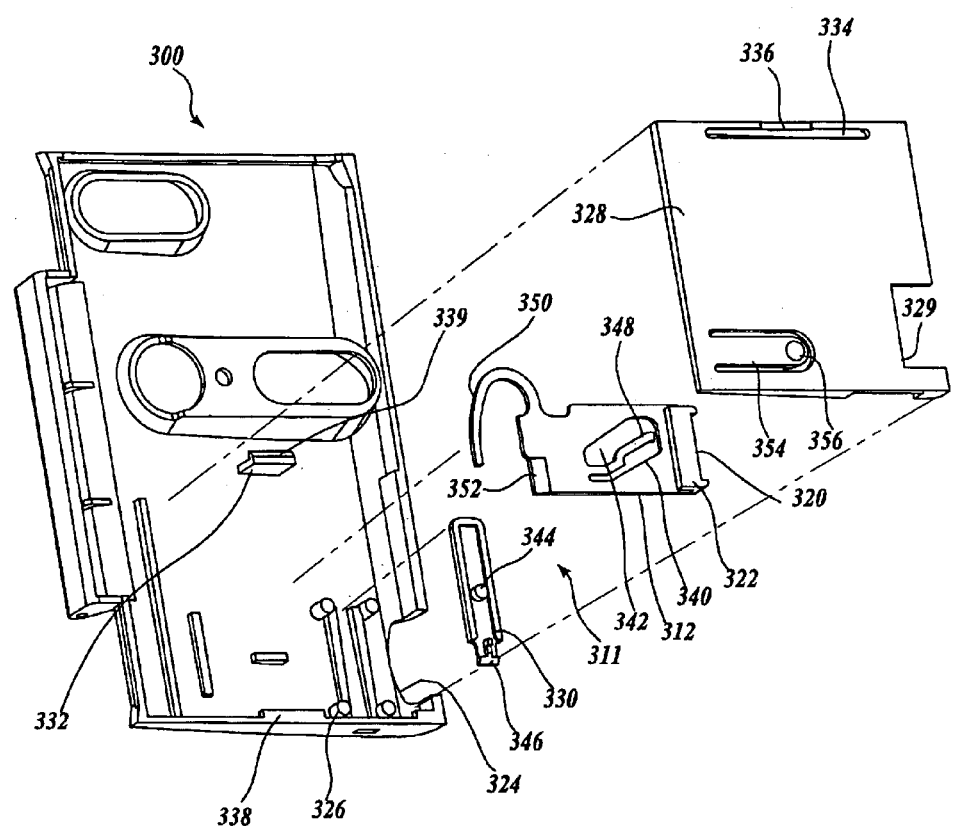
FIG. 9 shows an exploded view of the door of FIG. 7.

Referring now to FIGS. 7–9, an alternative embodiment of a door 300 used with the defibrillator 270 described above and illustrated herein will now be described in more detail. In this embodiment, the door 300 includes apertures 306, 304, and 308 through which only the user command buttons 271, 272 and 274 are accessible when the defibrillator 270 is in the AED mode. Accordingly, when the defibrillator 270 is powered up and the door 300 is in the closed position, the defibrillator is in the AED mode and only the AED command buttons are visible and accessible to the user. In addition to apertures 304, 306 and 308, the door 300 may also contain at least one aperture 310 for viewing status lights. The status lights may, for instance, indicate that the defibrillator 270 is powered and ready to deliver a shock therapy. It will be appreciated by those of ordinary skill in the art that the door 300 may contain any number of apertures deemed necessary for the industrial design of the defibrillator 270 depending on the number of features, e.g., command buttons, status indicators, etc. that are desired to be revealed to the user. For example, apertures 308 could be removed from the door 300 so as to hide the shock button 274 and provide a user interface for a fully automatic external defibrillator, or in other words, a third mode. Conversely, additional apertures may be provided for revealing additional features of the defibrillator 270. In addition to the number of apertures and buttons, those of ordinary skill in the art will also appreciate that the shape, size, configuration and location of the apertures and command buttons on the keypad 100 and/or door 300 may vary without departing from the spirit and scope of the present invention.

Referring now to FIG. 7, the door 300 of the defibrillator 270 includes an assembly 311 for opening the door 300. The assembly 311 includes an actuator slide 312, a latch 330, and cover 328 (cover 328 is shown in FIG. 8). As best illustrated in FIG. 9, one end of actuator slide 312 includes a transverse side wall having an inwardly extending flange 322. A slot or groove 320 is formed in the transverse side wall, and is suitably dimensioned for receiving a finger, and especially the thumb, of the user. The user presses the slot 320 to release a latch 330, which in turn, opens the door 300. Accordingly, the slot 320 protrudes through an opening 324 located on the lower portion of door 300, as illustrated in FIG. 7.

Referring now to FIG. 9, an exploded view of an actuator assembly 311 from the back side of door 300, the actuator slide 312, latch 330, and cover 328 are shown. Actuator slide 312 is mounted on door 300, such that the end of the actuator slide 312 protrudes through the opening 324 of the door when assembled. Actuator slide 312 is held in place to door 300 by cover 328, which retains the actuator slide within the door 300. Clips 332 and 338 molded onto door 300 retain cover 328 and allows actuator slide 312 to move in a horizontal direction, as will be described in more detail below.

The actuator slide 312, cover 328, and latch 330 cooperate with each other to provide a closing mechanism for the door 300. Latch 330 is located on the back side of door 300. Detailing on door 300, such as posts 326, help guide the latch 330 in vertical movement. Latch 330 is held to door 300 by cover 328. Latch 330 includes a chamfer 346 located on the lower end of latch 330 so as to engage a hole in the defibrillator device bezel (not shown) to secure the door 300 in a closed position. Latch 330 also includes a post 344 located approximately in the middle of the latch that engages the actuator slide 312, as will be described in more detail below. Latch 330 is thus constrained to move in a vertical direction by posts 326 on door 300.

Referring still to FIG. 9, the cover 328 is mounted to the door 300 such that actuator slide 312 and latch 330 are substantially concealed by cover 328. As shown in FIG. 9, the cover 328 includes a rectangular-shaped slot 329 positioned at its lower end. The slot 329 is suitably dimensioned to allow the flange portion 322 of the actuator slide 312 to translate within the slot 329 so that the latch may be released, and the door may be opened. Cover 328 is held to door 300 by clip 332 located on the back side of door 300. Clip 332 has an upturned lip end 339 that engages a horizontal aperture 334 and a groove 336 on the cover 328. On the bottom edge of door 300, another clip 338 is provided to retain cover 328 in position, along with clip 332. Thus, cover 328 helps to retain actuator slide 312 and latch 330 in position on the door 300, as shown in FIG. 8.

Returning to FIG. 9, the actuator slide 312 has an angled guide edge 340 formed within an aperture 342 to receive the post 344 of the latch 330. Post 344 is formed from latch 330 and projects outwardly so that a lower surface of the post 344 rides on the upper surface of guide edge 340. As the user presses the slot 320 and the actuator slide 312 is moved horizontally in a direction toward the hinged side of the door, the guide edge 340 pushes against post 344. Latch 330, being constrained to move in a vertical direction, rises to raise chamfer 346, thusly releasing the door 300.

Actuator slide 312 also includes spring 348 formed within the aperture 342 that is pushed upward by the latch when door 300 is being closed. Tensioned spring 348 biases latch 330 downward so that latch 330 snaps back forcibly to engage the device bezel. A second spring 350 formed integrally with the actuator slide 312 biases actuator slide 312 away from the hinged side of the door and opposes movement when the user pushes against the slot 320 from the outside of the door 300.

Actuator slide 312 further includes a ramp 352 tapering inwardly from the back side of the slide 312 to face the front side of the cover 328. In turn, cover 328 includes a ramp (not shown) located on a flexible cutout tongue 354 that faces the ramp 352 on actuator slide 312. A hemispherical bump 356 is also located on the flexible cutout tongue 354 on the side opposite of the cover ramp (not shown). Slide ramp 352 and cover ramp (not shown) have angled edges that ride against one another. The cover 328 is stationary as the actuator slide 312 is moved toward the hinged side of the door, and the ramps slide against one another, such that flexible tongue 354 moves in a direction away from the door 300 and toward the defibrillator 270. As the actuator slide 312 continues to move toward the hinged side of the door, the bump 356 is further pushed backwards and presses against an unmarked manual mode entry button 258 (FIG. 3) located on the user interface panel 100 of the defibrillator 270. Activation of the manual mode entry button 258 by the assembly 311 while the door 300 is in the closed position places the defibrillator in the manual mode. In one actual embodiment of the present invention, the manual mode button 258 remains unmarked, so as not to confuse the more experienced user upon opening of the door by perhaps providing an indication that an additional button must be pressed to switch modes.

The assembly 311 has four states: (1) When the door 300 is closed, the actuator slide 312 protrudes from the opening 324 in the door 300, the slide spring 350 is relaxed, and the latch 330 is in an extended position, engaging a hole in the device bezel. (2) When the door 300 is open, the actuator slide 312 protrudes from the opening 324 in the door 300, the slide spring 350 is relaxed, the latch 330 is in an extended position, and the door may be rotated up to about 270° from its closed position, and is resting against the side of the defibrillator. (3) When the door is being opened, i.e., the actuator slide 312 being moved to the right by the user when facing the defibrillator, the slide 312 is positioned right within the opening 324 in the door, the slide spring 350 is flexed, the ramp 352 on the back of the slide 312 engages with a ramp on the cover 328, causing the tongue 354 to flex, pushing the bump 356 against the manual mode button 258 (FIG. 3). The pressure of the bump 356 on the keypad 100 "pre-loads" the door with an outward force, and the post 344 on the latch 330 has ridden up the angled edge 340 in the actuator slide aperture 342. This moves the latch 330 vertically to its fully raised position, allowing the door 300 to spring open due to the pre-loading of the door. (4) In the fourth state, when the door 300 is being pressed closed by the user, the slide 312 protrudes from the opening 324 in the door. The slide spring 350 is relaxed, and the chamfer 346 on the latch 330 rides against the device bezel. This causes the latch 330 to move vertically, and post 344 pushes against the spring member 348 in the actuator slide aperture 342. The pressure against the spring member 348 by post 344 causes the latch 330 to return to an extended position as soon as the chamfer 346 moves into line with the hole in the bezel.

A door constructed according to either embodiment described above makes the manual mode button 258 (FIG. 3) accessible while the door is closed via the actuator slide 212 or 312, which changes the mode of the defibrillator from AED to manual mode. Concurrently with or shortly following the change of mode, the door latch is released, allowing the door to open and reveal the manual mode command buttons hidden beneath it. For clarity, the remaining description will be described with references to door 200. However, it will be appreciated by those skilled in the art that door 300 may also be utilized to change the mode of the defibrillator from AED to manual mode.

Returning to FIG. 3, the door 200 conceals a user interface panel or keypad 100 having the manual and AED mode command buttons. While softkeys may be used, buttons are used in the actual embodiment of the present invention shown in FIG. 3. The user interface panel 100 includes a plurality of manual buttons 262, 264 and 266 which are to be used while the defibrillator is in the manual mode. Manual mode button 258 is the mode changing button which is activated with the assembly 211 when the door is in the closed position. However, as noted above, the keypad 100 may contain any number of buttons for controlling or operating the defibrillator in manual mode. In yet other embodiments and as noted above, the user interface panel could include ports for the other medical accessories and sensors which may be attached to the defibrillator. Accordingly, if desired, the user interface of the defibrillator 270 could be made devoid of any and all controls, features, etc. not necessary or desired by an inexperienced responder in AED mode. Entering into the manual mode can also trigger other changes which affect the operation of the defibrillator. For instance, the electrocardiogram ("ECG") feature may be activated upon the display 102 to assist the experienced user in delivery of the appropriate shock therapy, while features which aid the inexperienced or infrequent user, e.g., visual CPR prompts, are turned off or temporarily hidden from the inexperienced operator.

A door constructed in accordance with the present invention presents numerous advantages. The door provides an uncluttered user interface for a less experienced user; the door conceals the manual mode command buttons; and the door still provides access to a manual mode button while the door is closed. Accordingly, the risk of an inexperienced user unintentionally opening the door 200 and placing the defibrillator in manual mode and/or revealing manual mode command buttons that could be confusing to the inexperienced user, is substantially reduced.

Figure 10:
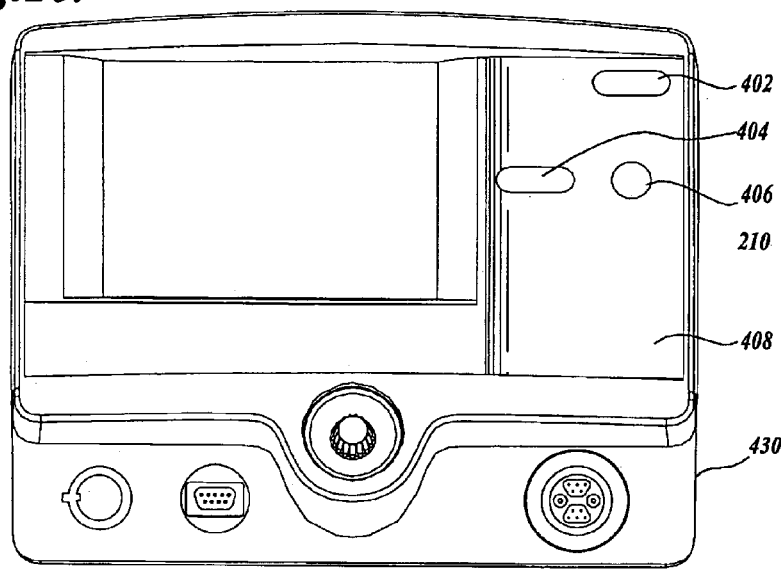
FIG. 10 shows a schematic representation of another embodiment of the defibrillator of FIG. 1 having AED mode command buttons on the front side of the door.
Figure 11:
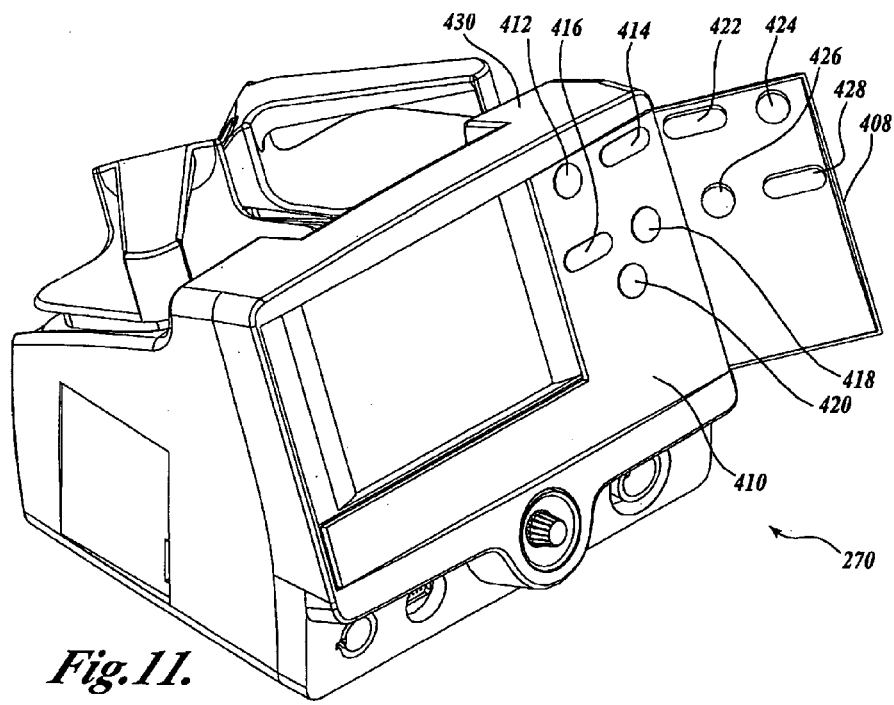
FIG. 11 shows a schematic representation of the defibrillator of FIG. 10 when the door is opened, revealing manual mode buttons.

FIGS. 10 and 11 are a schematic representation of a defibrillator 430 and a door 408 constructed in accordance with another actual embodiment of the present invention. As shown in FIG. 10, the AED command buttons 402, 404 and 406 are located on the outside of the door 408 itself rather than on a keypad beneath it. The defibrillator 430 and door 408 are equipped with a sensor such as a Hall effect switch or reed relay switch (not shown) which detects the opening of the door 408 and puts the defibrillator into the manual mode. It will be appreciated, however, that the defibrillator of this embodiment may be equipped with an actuator slide mechanism and manual mode entry button as described above so as to enter manual mode.

As shown in FIG. 11, a user interface panel or keypad 410 is concealed by the door 408 containing several manual user command buttons 412–420. Also, located on the rear side of the door 408 are several more manual user command buttons 422–428. It will be appreciated that the door 408 may contain any number of manual mode command buttons to control various defibrillator functions and features, e.g., charge, energy select, cardio-synchroversion, alarms, etc. When the door 408 is rotated outwardly, the manual mode command buttons 412–428 are visible, both on the rear side of the door 408 and on the keypad 410. Hence, the manual mode command buttons are concealed behind the door when the door is closed. As in the previous embodiment, the embodiment depicted in FIGS. 10 and 11 presents an inexperienced user with an uncluttered appearance while providing sophisticated manual features for the more experienced user, i.e., the manual mode command buttons being concealed by the door, and a door which changes the mode of the defibrillator quickly and easily.

Figure 12:
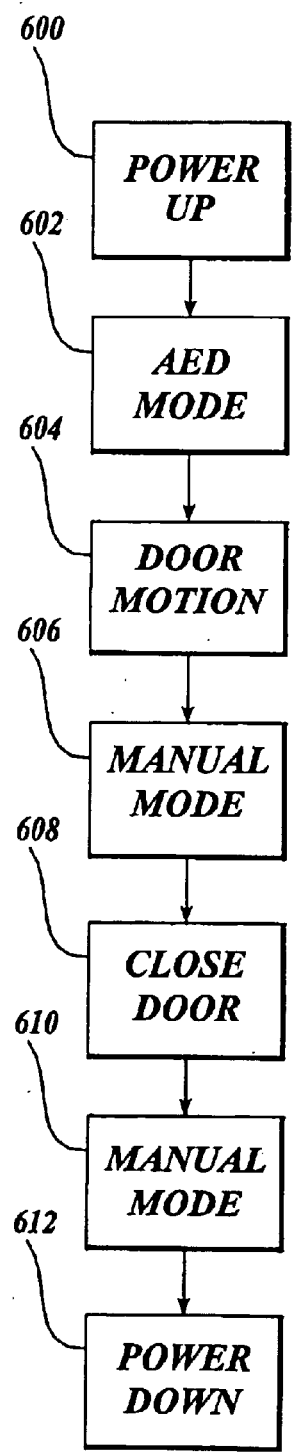
FIG. 12 shows a flowchart of the operation of a defibrillator formed in accordance with the present invention.

Referring now to FIG. 12, a flow chart is illustrated indicating the operation of the mode changing feature upon power up of the defibrillator with the door in the closed position. In a block 600, the defibrillator powers up—normally in response to depression of the "on" button 271. Next, the defibrillator enters the AED mode in a block 602. This is done regardless of whether the door is in the open state or the closed state, or even if the door is missing. This is a safety feature used to put the burden on the expert user to place the defibrillator in the manual mode.

Under normal circumstances, the door will most likely be closed when powering up, therefore, an action such as unlatching or opening the door and depressing the manual access button 258 via the actuator assembly 211 in block 604, will send the defibrillator into manual mode, as shown in block 606. While in manual mode, several functions may be enabled, such as calling the ECG waveform display feature while disabling or hiding other features which are not necessary while in the manual mode.

If the door has been opened intentionally, the most likely event to occur next under normal circumstances is to close the door 608, i.e., after therapy has been delivered by the experienced user. This action, however, causes the defibrillator to remain in the manual mode, represented by block 610.

The next most likely event is that the defibrillator will be powered down by the user by depressing the power button in block 612. When the defibrillator is powered up again, the defibrillator starts and returns to the AED mode, as shown in blocks 600 and 602, again placing the burden on the experienced user to affirmatively change from the AED mode into the manual mode. Presumably, the experienced user will be more familiar with the features of the defibrillator, therefore the startup failsafe state is the AED mode. Although FIG. 12 shows the order of operation of the mode changing feature in one actual embodiment of the present invention, those of ordinary skill in the art will appreciate that the order of certain steps can be changed, and that certain steps themselves can be changed and/or added/deleted without departing from the spirit and scope of the present invention. For example, in another actual embodiment of the present invention, the defibrillator may power up in the manual mode and then time out to the AED mode if no further command buttons are pushed or action taken. As yet another example, the defibrillator could be powered down immediately or could return to AED mode upon closing the door.

Figure 13:
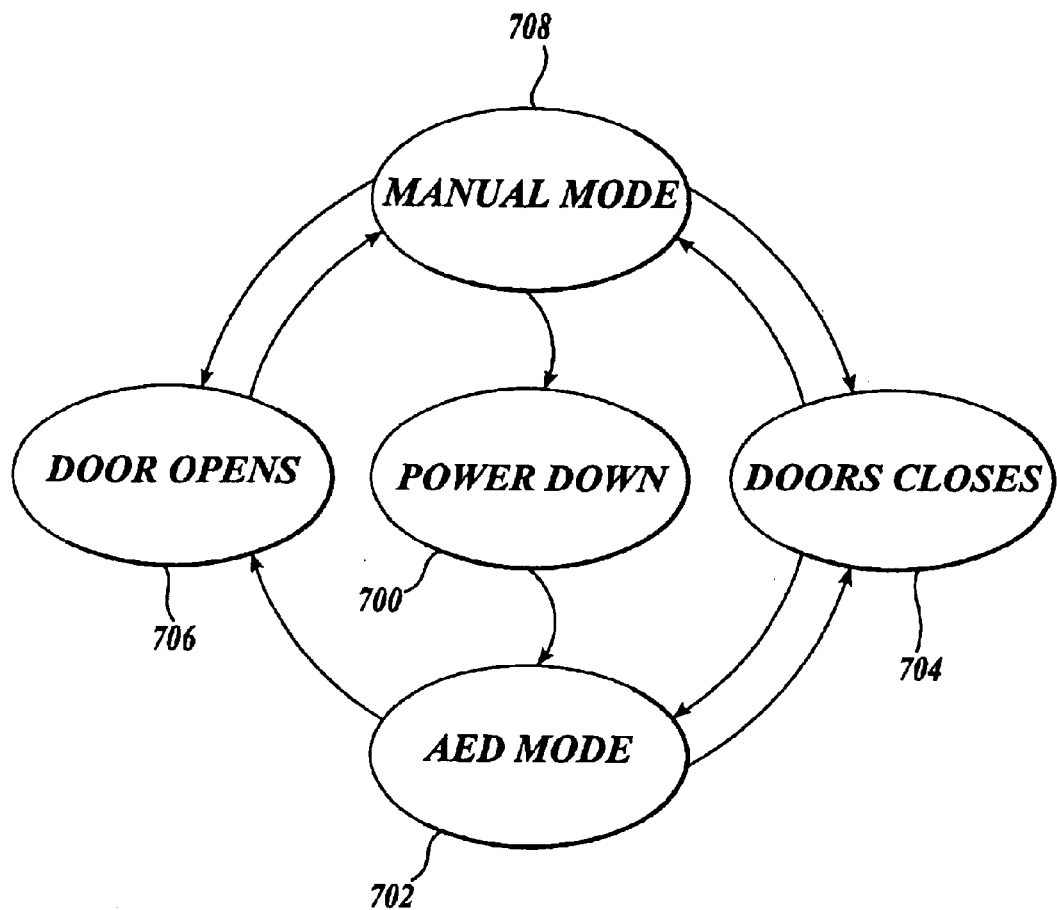
FIG. 13 shows a state diagram of the manual and AED modes of a defibrillator formed in accordance with the present invention.

Finally, referring to FIG. 13, a state diagram shows the various states of the multiple mode defibrillator formed in accordance with the present invention with the door in the open and closed position. If the defibrillator is in the powered down mode 700, powering up will put the defibrillator into AED mode 702 regardless whether the door is opened or closed. While in the AED mode 702, if the door had been open upon power up (i.e., the user presses the on button 271 while the door is open) and thereafter closed 704, the defibrillator stays in the AED mode 702. However, if the door is closed at power up, and thereafter opened 706 while in the AED mode 702, the defibrillator enters into the manual mode 708. Thereafter, while in the manual mode 708, closing 704 or opening 706 the door has no effect on the state or mode of the defibrillator, i.e., it remains in the manual mode 708 until the defibrillator is powered down 700 and is powered up again. Accordingly, the defibrillator exits the manual mode 708 to enter into the AED mode 702.

While the preferred embodiment of the invention has been illustrated and described, it will be appreciated that various changes can be made therein without departing from the spirit and scope of the invention. For example, to further secure the door in the closed position and prevent unintentional opening by an inexperienced user, the door may be equipped with a lock for which an experienced user holds a key, combination or other unlocking mechanism. Further, the door may be of any shape or configuration necessary to hide access to the manual mode command buttons while still revealing the AED mode command buttons there through. For example, a door can be constructed having an assembly for opening the door with the rib located near the edge of the door.

The embodiments of the invention in which an exclusive property or privilege is claimed are defined as follows:

1. A defibrillator having a first mode and a second mode; comprising:
    a mode changing switch; and
    a door that is operably coupled to the switch,
    wherein the switch sends the defibrillator from the first mode to the second mode when the door is opened, the defibrillator remains in the second mode when the door is subsequently closed, and the defibrillator returns to the first mode when the defibrillator is powered down and then powered up.

2. The defibrillator of claim 1, wherein the defibrillator returns to the first mode when the defibrillator is powered down and then powered up with the with the door in an open position.

3. The defibrillator of claim 1, wherein the door conceals input media for activating second mode user commands.

4. The defibrillator of claim 3, wherein the input media for activating second mode user commands are push buttons.

5. The defibrillator of claim 1, wherein the door has a first side, a second side, first input media for activating first mode user commands located on the first side of the door, and second input media for activating second mode user commands located on the second side of the door.

6. The defibrillator of claim 1, wherein the door has a plurality of apertures that allow a user to access input media for activating first mode user commands.

7. The defibrillator of claim 1, wherein the first mode is an automatic external defibrillator (AED) mode and second mode is a manual mode.

8. An external defibrillator comprising:
    first input media for operating the defibrillator in a manual mode;
    second input media for operating the defibrillator in an automatic external defibrillator (AED) mode; and
    a door coupled to the defibrillator that conceals said first input media and allows a user to access said second input media located beneath the door when the door is in a closed position.

9. The defibrillator of claim 8, further comprising a mode changing switch covered by the door when the door is in the closed position.

10. The defibrillator of claim 9, wherein the door further comprises an actuator assembly for giving access to the switch when the door is in the closed position.

11. The defibrillator of claim 9, wherein the switch is activated when the door is opened.

12. A method of using a defibrillator having a mode changing door, the method comprising:
    placing the defibrillator in a first mode based on power up of the defibrillator;
    placing the defibrillator in a second mode based on opening of the mode changing door;
    keeping the defibrillator in the second mode when the mode changing door is closed while the defibrillator is in the second mode; and
    returning the defibrillator to the first mode based on powering down and then powering up of the defibrillator.

13. The method of claim 12, wherein returning the defibrillator to the first mode based on powering down and then powering up the defibrillator comprises returning the defibrillator to the first mode based on powering down and then powering up with the mode changing door in an open position.

14. The method of claim 12, wherein the first mode is an AED mode and the second mode is a manual mode.

* * * * *